(12) United States Patent
Nakao et al.

(10) Patent No.: US 8,731,254 B2
(45) Date of Patent: May 20, 2014

(54) BIOLOGICAL SIGNAL DRAWING APPARATUS AND BIOLOGICAL SIGNAL DRAWING METHOD

(75) Inventors: Yoshiaki Nakao, Tokyo (JP); Kaoru Imajo, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 708 days.

(21) Appl. No.: 12/612,701

(22) Filed: Nov. 5, 2009

(65) Prior Publication Data

US 2010/0119130 A1 May 13, 2010

(30) Foreign Application Priority Data

Nov. 7, 2008 (JP) ................. 2008-286746

(51) Int. Cl.
 G06K 9/00 (2006.01)
 G06T 7/00 (2006.01)
 G06F 19/00 (2011.01)
(52) U.S. Cl.
 CPC ............ *G06T 7/0012* (2013.01); *G06F 19/321* (2013.01)
 USPC ........................................................ 382/128
(58) Field of Classification Search
 CPC ........................... G06T 7/0012; G06F 19/321
 USPC ........................................................ 382/128
 See application file for complete search history.

(56) References Cited

U.S. PATENT DOCUMENTS

| 5,673,702 A | 10/1997 | Albrecht |
| 2008/0243209 A1 | 10/2008 | Corndorf |

FOREIGN PATENT DOCUMENTS

| JP | 63-157064 A | 6/1988 |
| JP | 3-131226 A | 6/1991 |
| JP | 4-299261 A | 10/1992 |
| JP | 10-509331 A | 9/1998 |
| JP | 2006-4504 A | 1/2006 |

OTHER PUBLICATIONS

Fira M et al: "A New Compression Algorithm For ECG Signals" Computer As A Tool, 2005. The International Conference on Belgrade, Serbia and Montenegro Nov. 21-24, 2005, Piscataway, NJ, USA, vol. 1, Nov. 21, 2005, pp. 405-408, XP010916111 ISBN: 978-1-4244-0049-2.

Jacek M Leski: "Robust Weighted Averaging" IEEE Transactions on Biomedical Engineering, IEEE Service Center, Piscataway, NJ, US, vol. 49, No. 8, Aug. 1, 2002, pp. 796-804; XP011070366 ISSN 0018-9294.

(Continued)

*Primary Examiner* — Sheetal R Rangrej
(74) *Attorney, Agent, or Firm* — Sughrue Mion, PLLC

(57) ABSTRACT

A biological signal drawing apparatus draws biological signals as drawing points in time series. The biological signal drawing apparatus includes: a thinner performing a thinning process to thin a first number of the drawing points corresponding to the biological signals sampled in each pixel zone, to obtain a second number of the drawing points for each pixel zone, the second number being smaller than the first number; a calculator, after the thinning process is performed, calculating a parameter based on at least one difference of values of adjacent two of the drawing points included in a group that includes: a first drawing point being a center in time series in the group and having a first value; and at least one second drawing point preceding or succeeding the first drawing point in time series and having a second value; and a processor performing a process of: performing a weighted moving average calculation using the first value, the second value and the calculated parameter, to obtain a third value; and replacing the first value with the third value.

14 Claims, 9 Drawing Sheets

(56) References Cited

OTHER PUBLICATIONS

Extended European Search Report dated Dec. 29, 2009 issued in corresponding European Application No. 09174549.7-1265, 7 pages.
Communication dated Oct. 30, 2012 from the Japanese Patent Office in counterpart Japanese Application No. 2008-286746.
Communication dated Jan. 20, 2014, issued by the European Patent Office in corresponding Application No. 09174549.7.
Bataillou et al., "Weighted averaging using adaptive estimation of the weights," Signal Processing, Elsevier Science B.V., Jun. 1, 1995, vol. 44, Issue 1, 16 total pages.

BIOLOGICAL SIGNAL DRAWING APPARATUS AND BIOLOGICAL SIGNAL DRAWING METHOD

BACKGROUND OF THE INVENTION

The present invention relates to a biological signal drawing apparatus and method in which a waveform on the basis of a biological signal such as a brain wave signal is displayed on a screen such as a displaying device, or printed by a printer.

A biological signal waveform which is typified by an electroencephalogram or an electrocardiogram is output onto recording paper or the like by an ink recorder, and then used in clinical examination by doctor. Recently, moreover, a paperless electroencephalograph or electrocardiograph has been advanced, and a biological signal such as a brain wave signal is digitized, so that, for example, the digitized signal is sent to a displaying device and an electroencephalogram is displayed on a screen.

In a display in which such digital data are drawn on a screen, a line segment is expressed as a set of pixels, and therefore it is often that the impression of the waveform is different from that of a waveform which is drawn on recording paper by using an ink recorder that analogly performs drawing.

This is caused by the phenomenon that the elasticity and frequency characteristics of a pen of the ink recorder cause the pen not to be able to respond to very small noises, and in contrast even such noises are faithfully drawn in the drawing of the digital data on the screen.

Therefore, doctors who have reviewed an electroencephalogram on recording paper point out that an electroencephalogram displayed on a screen appears different from that on recording paper, and an electroencephalogram on recording paper in noiseless and looks clear. Therefore, it is requested to develop a biological signal drawing apparatus which can perform a waveform display that is similar to drawing on recording paper. There is a similar problem also in the case where a waveform is printed by a printer in addition to display.

In order to smoothly draw an electroencephalogram, it is contemplated that the smoothing technique is applied to the drawing. In the case where the smoothing technique is simply applied to the drawing, however, there is a possibility that smoothing affects waveform drawing of a characteristic change of a biological signal waveform, such as spikes in an electroencephalogram.

By contrast, in view of a problem that an abnormality cannot be found unless a waveform is printed out, a solution has been taken in which a format (a two-dimensional pattern) of recording paper is displayed on a monitor (see JP-T-10-509331). However, a waveform is drawn by a related-art technique, and the drawn waveform is not made close to a waveform which is drawn by an ink recorder (see JP-T-10-509331).

SUMMARY

It is therefore an object of the invention to provide a biological signal drawing apparatus which can perform waveform drawing that is close to a waveform which is drawn on recording paper by an ink recorder. It is another object of the invention to provide a biological signal drawing method which enables waveform drawing that is close to a waveform which is drawn by an ink recorder, to be performed.

In order to achieve the object, according to the invention, there is provided a biological signal drawing apparatus, drawing biological signals as drawing points in time series, the biological signal drawing apparatus comprising:

a thinner which performs a thinning process to thin a first number of the drawing points corresponding to the biological signals sampled in each pixel zone, to obtain a second number of the drawing points for each pixel zone, the second number being smaller than the first number;

a calculator which, after the thinning process is performed, calculates a parameter based on at least one difference of values of adjacent two of the drawing points included in a group that includes:

a first drawing point which is a center in time series in the group and which has a first value; and at least one second drawing point which precedes or succeeds the first drawing point in time series and which has a second value; and a processor which performs a process of:

performing a weighted moving average calculation using the first value, the second value and the calculated parameter, to obtain a third value; and replacing the first value of the first drawing point with the third value.

After the thinning process is performed, the drawing points in each pixel zone may include drawing points having maximum and minimum values in each pixel zone.

The parameter may be calculated based on an absolute value of the at least one difference of the values of adjacent two of the drawing points included in the group.

The parameter may be calculated by using an exponential function.

The at least one second point may include two preceding points and two succeeding points with respect to the first point in time series, and the parameter may be calculated with following calculations:

$$\text{AbsDiff\_Sum} = |\text{Diff}_{-1}| + |\text{Diff}_{-2}| + |\text{Diff}_{+2}| + |\text{Diff}_{+1}|;$$

$$\text{AbsDiff} = (\text{AbsDiff\_Sum})^3;\text{ and}$$

$$\text{Smooth\_Coef} = 0.2 \exp(-\text{AbsDiff} \times K),$$

where the parameter is Smooth_Coef, absolute values of differences of values of adjacent two of the preceding drawing points, the first drawing point and the succeeding drawing points are $|\text{Diff}_{-2}|$, $|\text{Diff}_{-1}|$, $|\text{Diff}_{+1}|$, and $|\text{Diff}_{+2}|$, respectively, and a coefficient is K.

The preceding drawing points may include a first preceding drawing point and a second preceding drawing point, the succeeding drawing points may include a first succeeding drawing point and a second succeeding drawing point, the second preceding drawing point, the first preceding drawing point, the first drawing point, the first succeeding drawing point and the second succeeding drawing point may be arranged in this order in time series, and the weighted moving average calculation may be performed with a following calculation:

$$V_0\_\text{New} = V_{-2} \times \text{Smooth\_Coef} + V_{-1} \times \text{Smooth\_Coef}$$

$$+ V_0 \times (1 - 4\text{Smooth\_Coef})$$

$$+ V_{+1} \times \text{Smooth\_Coef} + V_{+2} \times \text{Smooth\_Coef},$$

where the first value of the first drawing point is $V_0\_\text{New}$, and values of the second preceding drawing point, the first preceding drawing point, the first succeeding drawing point and the second succeeding drawing point are $V_{-2}$, $V_{-1}$, $V_{+1}$, and $V_{+2}$, respectively.

The biological signal drawing apparatus may further comprise an antialiasing unit which performs antialiasing to a waveform drawn by the drawing points to which the process having been performed.

According to the invention, there is also provided a method of drawing biological signals as drawing points in time series, the method comprising:

performing a thinning process to thin a first number of the drawing points corresponding to the biological signals sampled in each pixel zone, to obtain a second number of the drawing points for each pixel zone, the second number being smaller than the first number;

after the thinning process is performed, calculating a parameter based on at least one difference of values of adjacent two of the drawing points included in a group that includes:

a first drawing point which is a center in time series in the group and which has a first value; and at least one second drawing point which precedes or succeeds the first drawing point in time series and which has a second value; and performing a process of:

performing a weighted moving average calculation using the first value, the second value and the calculated parameter, to obtain a third value; and replacing the first value of the first drawing point with the third value.

After the thinning process is performed, the drawing points in each pixel zone may include drawing points having maximum and minimum values in each pixel zone.

The parameter may be calculated based on an absolute value of the at least one difference of the values of adjacent two of the drawing points included in the group.

The parameter may be calculated by using an exponential function.

The at least one second point may include two preceding points and two succeeding points with respect to the first point in time series, and the parameter may be calculated with following calculations:

$$\text{AbsDiff\_Sum} = |\text{Diff}_{-1}| + |\text{Diff}_{-2}| + |\text{Diff}_{+2}| + |\text{Diff}_{+1}|;$$

$$\text{AbsDiff} = (\text{AbsDiff\_Sum})^3; \text{ and}$$

$$\text{Smooth\_Coef} = 0.2 \exp(-\text{AbsDiff} \times K),$$

where the parameter is Smooth_Coef, absolute values of differences of values of adjacent two of the preceding drawing points, the first drawing point and the succeeding drawing points are $|\text{Diff}_{-2}|$, $|\text{Diff}_{-1}|$, $|\text{Diff}_{+1}|$, and $|\text{Diff}_{+2}|$, respectively, and a coefficient is $K$.

The preceding drawing points may include a first drawing preceding point and a second drawing preceding point, the succeeding drawing points may include a first succeeding drawing point and a second succeeding drawing point, the second preceding drawing point, the first preceding drawing point, the first drawing point, the first succeeding drawing point and the second succeeding drawing point may be arranged in this order in time series, and the weighted moving average calculation may be performed with a following calculation:

$$V_0\_\text{New} = V_{-2} \times \text{Smooth\_Coef} + V_{-1} \times \text{Smooth\_Coef}$$

$$+ V_0 \times (1 - 4\text{Smooth\_Coef})$$

$$+ V_{+1} \times \text{Smooth\_Coef} + V_{+2} \times \text{Smooth\_Coef},$$

where the first value of the first drawing point is $V_0\_\text{New}$, and values of the second preceding drawing point, the first preceding drawing point, the first succeeding drawing point and the second succeeding drawing point are $V_{-2}$, $V_{-1}$, $V_{+1}$, and $V_{+2}$ respectively.

The method may further comprise performing antialiasing to a waveform drawn by the drawing points to which the process having been performed.

DETAILED DESCRIPTION OF EMBODIMENTS

Figure 1:
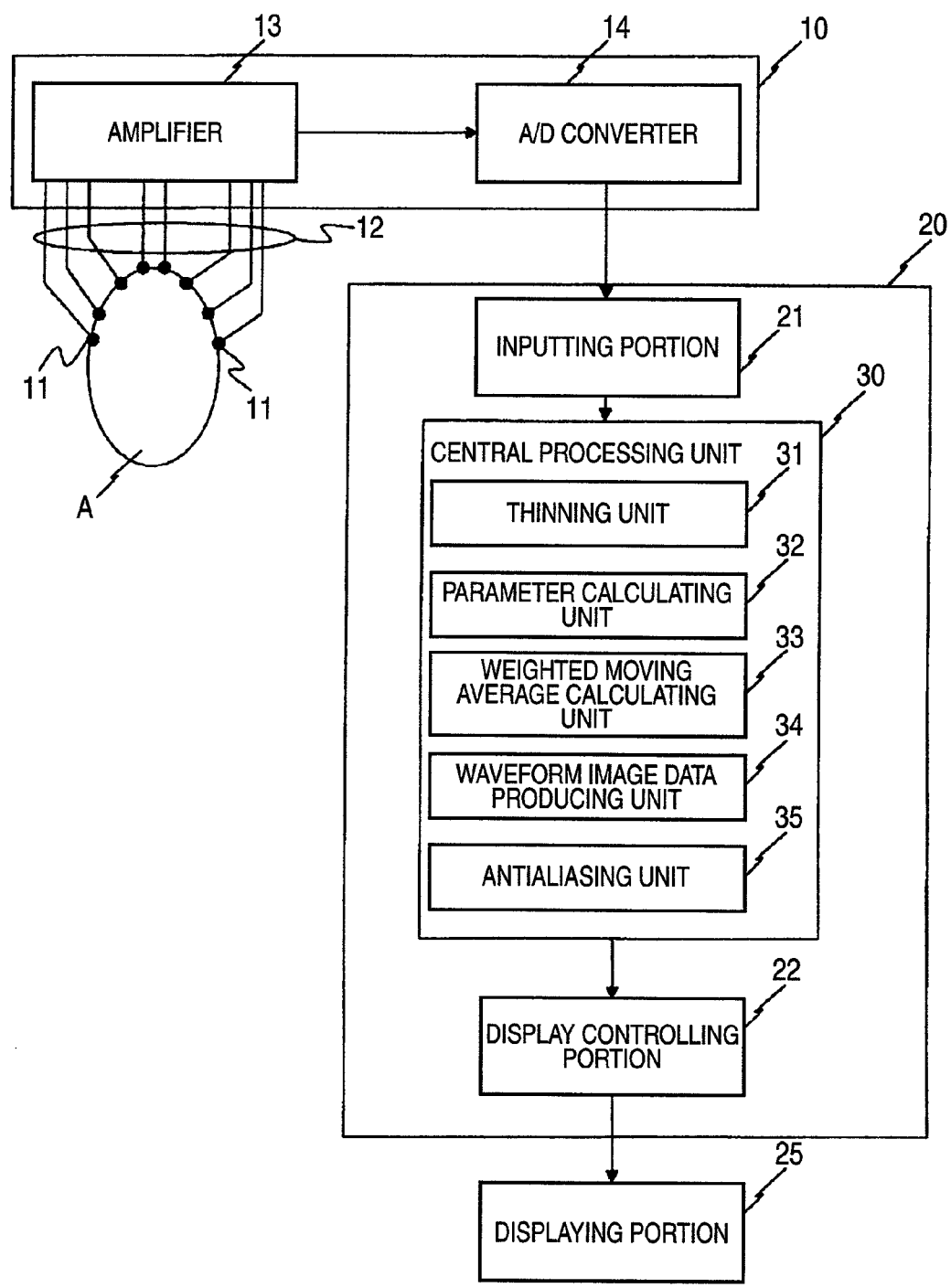
FIG. 1 is a block diagram of an electroencephalograph which is an embodiment of a biological signal drawing apparatus of the present invention.

Hereinafter, an embodiment of the biological signal drawing apparatus, method, and program of the invention will be described with reference to the accompanying drawings. FIG. 1 shows the configuration of an electroencephalograph which is an embodiment of a biological signal drawing apparatus of the present invention. A plurality of electrodes 11 including a reference electrode are attached to the head of a subject A, lead wires 12 are connected to the electrodes 11, respectively, and the lead wires are connected to an amplifier 13 of an electrode junction box 10. Namely, a brain wave signal which is induced in one of the electrodes 11 is sent to the amplifier 13 through the corresponding one of the lead wires 12, and then subjected to predetermined amplification in the amplifier 13.

An A/D converter 14 is connected to the amplifier 13 so that the brain wave signal amplified in the amplifier 13 is converted in the A/D converter 14 to a digital signal at a predetermined sampling frequency (for example, 200 Hz, 500 Hz, or 1,000 Hz). The digitized brain wave signal is sent to an inputting portion 21 of a main unit 20. The main unit 20 includes a central processing unit 30 and a display controlling portion 22 in addition to the inputting portion 21.

The inputting portion 21 performs a process of montaging the brain wave signal (a signal production due to combination of the electrodes), and further performs a sensitivity process and a filter process to the brain wave signal to execute removal of noises and unwanted components, and the like.

The central processing unit 30 performs an electroencephalogram waveform image data by using the digitized brain wave signal which is processed by the inputting portion 21, and is configured by a computer. The central processing unit 30 includes a thinning unit 31, a parameter calculating unit 32, a weighted moving average calculation processing unit 33, a waveform image data producing unit 34, and an antialiasing unit 35.

The waveform image data producing unit 34 sets an axis of the value of a biological signal in the vertical direction. The waveform image data producing unit 34 arranges pixel zones in the lateral direction and sets the same as a time axis. The waveform image data producing unit 34 repeats, in the time axis direction, a process of allocating respective first numbers of sampled biological signals to the pixel zones and setting the value of each biological signal as a drawing point to perform drawing in each of the pixel zones. In the embodiment, the first number is set to 3.

The thinning unit 31 performs a thinning process to thin the first number of drawing points in each pixel zone in the time axis direction, to obtain a second number of drawing points for each pixel zone. The second number is smaller than the first number. In the embodiment, the thinning unit 31 executes a process of leaving the maximum and minimum values of the drawing points.

The parameter calculating unit 32 performs a process of, based on a difference of values of adjacent drawing points by using values of a plurality of drawing points which precede or succeed a drawing point of interest (hereinafter, often referred to as an interest drawing point) in a case where drawing points as a result of the thinning process by the thinning unit 31 are arranged in time series, performing a predetermined calculation to calculate a parameter, while sequentially shifting the interest drawing point. In the embodiment, the parameter calculating unit 32 performs the process by using the values of two drawing points which precede the interest drawing point in time series, and two drawing points which succeed the interest drawing point in time series.

When absolute values of differences of values of adjacent drawing points of the two preceding and two succeeding drawing points with respect to the interest drawing point are $|Diff_{-2}|$, $|Diff_{-1}|$, $|Diff_{+1}|$, and $|Diff_{+2}|$, respectively, and a coefficient is K, the parameter calculating unit 32 in the embodiment performs following Expression 1 to obtain a parameter Smooth_Coef.

$$AbsDiff\_Sum = |Diff_{-1}| + |Diff_{-2}| + |Diff_{+2}| + |Diff_{+1}|$$

$$AbsDiff = (AbsDiff\_Sum)^3$$

$$Smooth\_Coef = 0.2 \exp(-AbsDiff \times K) \quad \text{(Expression 1)}$$

In order to determine the degree of the variation of the waveform, the parameter Smooth_Coef is calculated by using the absolute value of the difference between the value of the interest drawing point and that of an adjacent drawing point. In order to apply weak smoothing to a portion where the variation of the waveform is large, and strong smoothing to a portion where the variation of the waveform is small, furthermore, the parameter Smooth_Coef is calculated by using an exponential function in which a factorial (for example, cube) of the absolute value of the difference of adjacent drawing points is input.

The weighted moving average calculation processing unit 33 performs a process of performing a weighted moving average calculation by applying the parameter obtained in the parameter calculating unit 32 to the value of the interest drawing point and values of at least one drawing points which precede or succeed the interest drawing point, and replacing the value of the interest drawing point with a value of a result of the weighted moving average calculation, while sequentially shifting the interest drawing point.

The antialiasing unit 35 performs antialiasing to a waveform which is produced by the waveform image data producing unit 34 on the basis of a result of the process by the weighted moving average calculation processing unit 33. The antialiasing unit 35 in the embodiment is configured by GDI+ from Microsoft Corporation (Microsoft is a registered trademark).

Image data of the waveform produced by the waveform image data producing unit 34 are sent to the display controlling portion 22. The display controlling portion 22 displays the image data on a displaying portion 25 configured by LEDs or the like.

Figure 2:
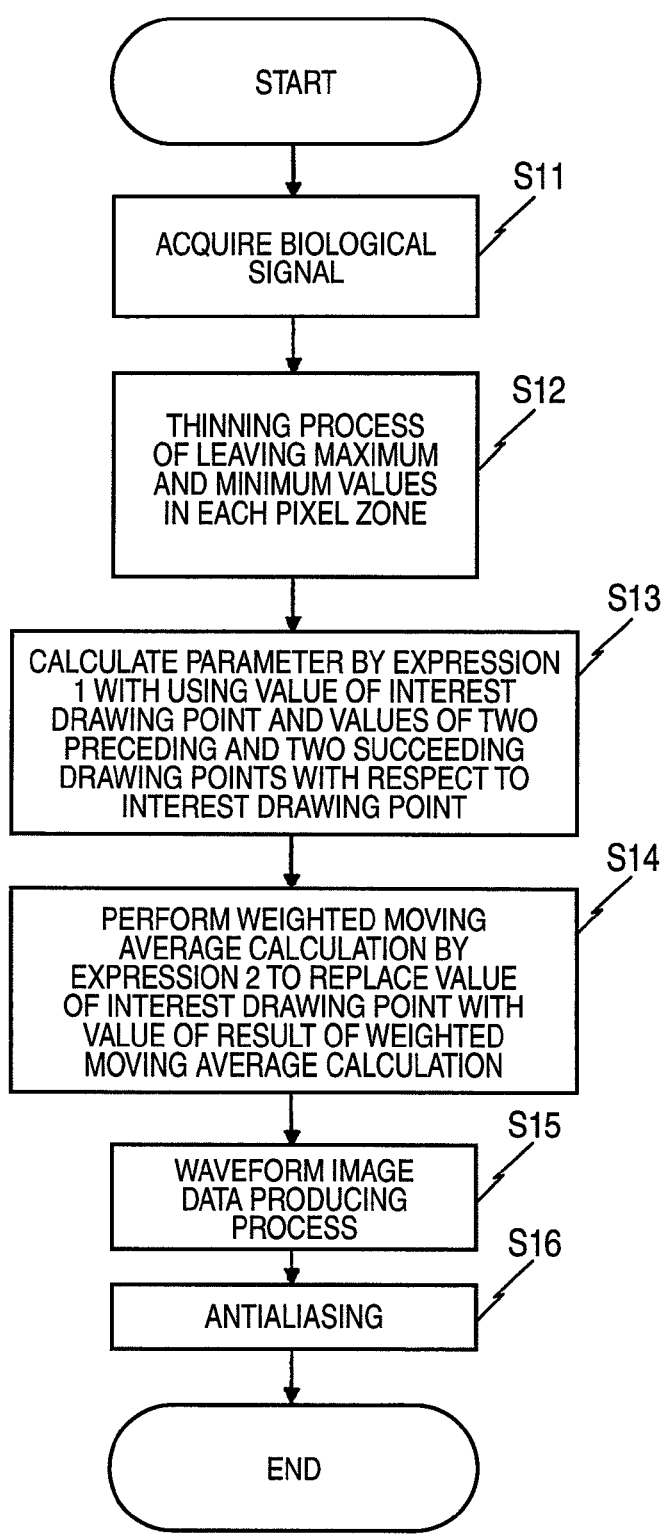
FIG. 2 is a flowchart illustrating operation of the electroencephalograph.

In the above-described configuration, the thinning unit 31, the parameter calculating unit 32, the weighted moving average calculation processing unit 33, the waveform image data producing unit 34, and the antialiasing unit 35 are realized by executing programs corresponding to the flowchart shown in FIG. 2, on the computer. Therefore, the operation will be described with reference to the flowchart shown in FIG. 2.

Figure 3:
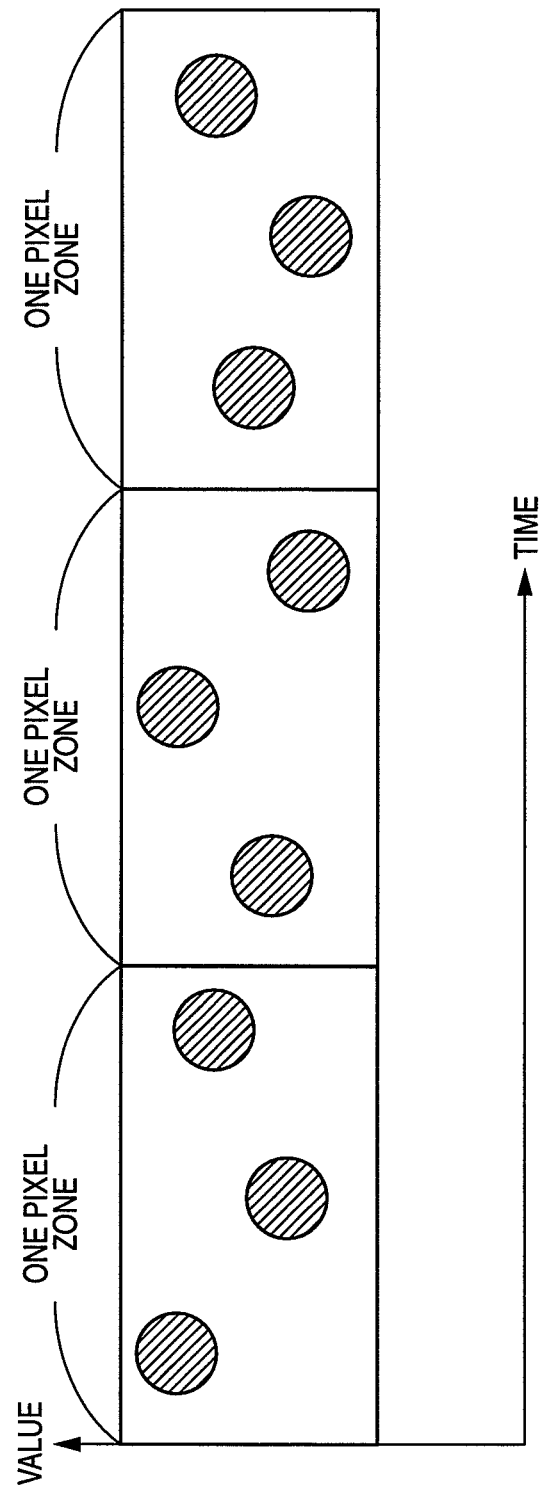
FIG. 3 is a view illustrating drawing points included in each pixel zone, in a biological signal sampled by the electroencephalograph.
Figure 6A:
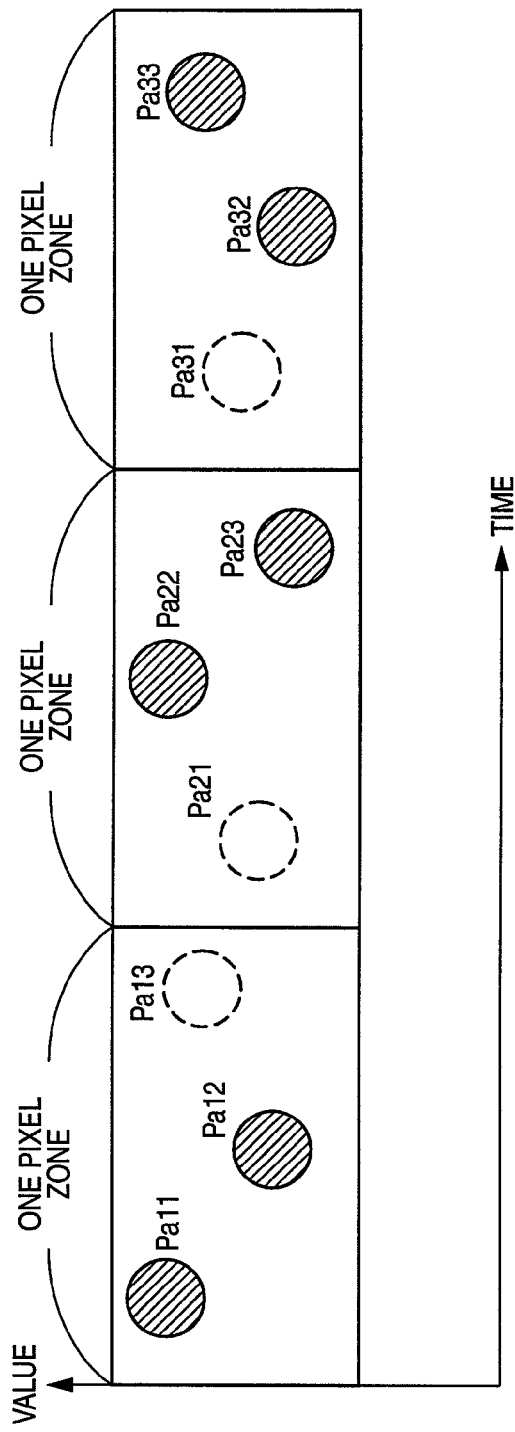
FIGS. 6A and 6B are views illustrating an operation of producing drawn image data in the electroencephalograph.

First, a biological signal is acquired from the inputting portion 21 (S11), and the thinning process of leaving the maximum and minimum values in each pixel zone is conducted (S12: thinning step). When a sampling rate is set so that three drawing points are included in each pixel zone as shown in FIG. 3, for example, two values, or the maximum and minimum values are left in each pixel zone. The drawing points which are indicted by the broken lines in FIG. 6A are thinned out from the drawing points shown in FIG. 3. As a result, the waveform image data producing unit 34 draws two drawing points in each pixel zone, so that the process load can be reduced.

Figure 4:
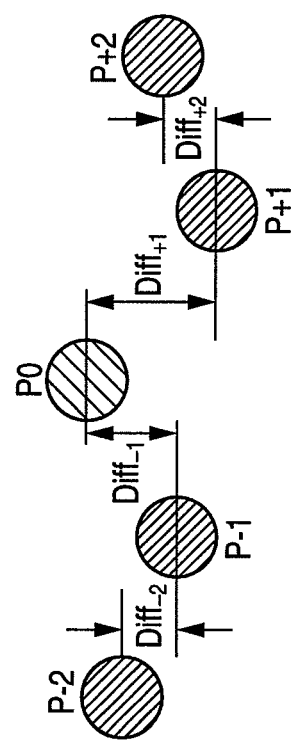
FIG. 4 is a view illustrating values of differences between an interest drawing point and adjacent drawing points that are used in a parameter calculating operation of the electroencephalograph.

Next, for a row of the drawing point obtained as a result of the thinning, the parameter is calculated by Expression 1 above, with using the value of the interest drawing point and the values of two preceding and two succeeding drawing points with respect to the interest drawing point (S13: parameter calculating step). FIG. 4 shows a manner where, with respect to the interest drawing point P0, two drawing points P−1, P−2 exist preceding the interest drawing point P0 in time series, two drawing points P+1, P+2 exist succeeding the interest drawing point P0 in time series, and the values of differences between adjacent two of the drawing points P−2, P−1, P0, P+1 and P+2 are $Diff_{-2}$, $Diff_{-1}$, $Diff_{+1}$, and $Diff_{+2}$.

The step of calculating the parameter is performed on all drawing points while sequentially shifting the interest drawing point. Empirically, it is preferable that the constant K is about 0.001.

Next, by using the parameter Smooth_Coef calculated in the parameter calculating step, a weighted moving average calculation is performed by Expression 2 below to replace the value of the interest drawing point with the value of a result of the weighted moving average calculation (S14: weighted moving average calculation processing step).

$$V_0\_New = V_{-2} \times Smooth\_Coef + V_{-1} \times Smooth\_Coef$$

$+V_0 \times (1-4\text{Smooth\_Coef})$ $+V_{+1} \times \text{Smooth\_Coef} + V_{+2} \times \text{Smooth\_Coef}$ (Expression 2)

The weighted moving average calculation processing step is conducted while being corresponded to the interest drawing point in the parameter calculating step. Next, a waveform image data producing process is conducted (S15: waveform image data producing process step). In step S15, an axis of the value of a drawing point is set in the vertical direction, pixel zones are arranged in the lateral direction and set as a time axis, and a process of allocating respective predetermined numbers (in the example, two or maximum and minimum) of drawing points to the pixel zones, setting the values of the drawing points as drawing points, and performing drawing in each pixel zone is repeated in the time axis direction.

Figure 5A:
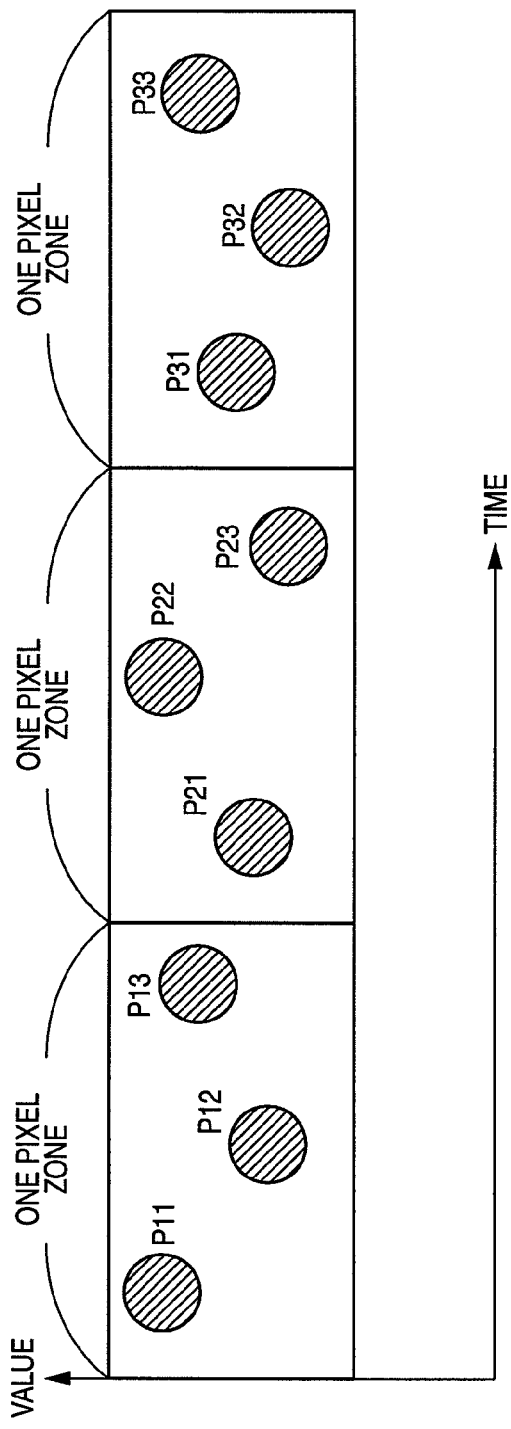
FIGS. 5A and 5B are views illustrating the parameter calculating operation of the electroencephalograph.
Figure 5B:
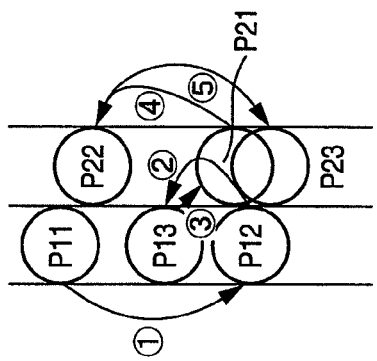

When three drawing points are sampled in one pixel zone as shown in FIG. 5A and the drawing points are drawn as they are, for example, the waveform image data producing process step functions in the following manner. As shown in FIG. 5B in which the order is indicated by a number in a circle, P11 is drawn in the same pixel zone, drawing in which a filling process is performed from P11 to P12 is conducted, and drawing in which a filling process is performed from 212 to P13 is then conducted. Next, drawing is conducted while the time axis is shifted to the pixel zone which is adjacent to the pixel zone of P11, P12, and P13. After shifting, P21 is first drawn, drawing in which a filling process is performed from P21 to P22 is conducted, and drawing in which a filling process is performed from P22 to P23 is then conducted. Subsequently, the drawing process is repeated in a similar manner.

Figure 6B:
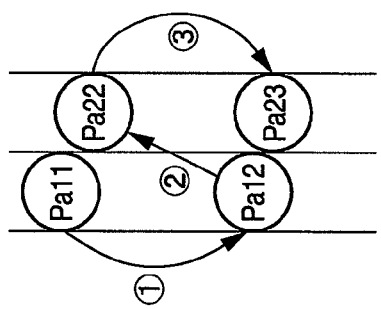

In the embodiment, by contrast, the maximum and minimum drawing points are obtained from three drawing points in one pixel zone shown in FIG. 6A, and the drawing point indicated by the broken line is thinned out. As described above, furthermore, the weighted moving average calculating process is performed so that the pixel value is converted by Expression 2. In FIG. 6A, the drawing points which are converted as a result of the weighted moving average calculating process are shown as Pa11, Pa12, Pa22, Pa23, Pa32, and Pa33. In this case, the waveform image data producing process step functions in the following manner. The converted two points in each pixel zone shown in FIG. 6A are drawn. As shown in FIG. 6B in which the order is indicated by a number in a circle, Pa11 is drawn in the same pixel zone, and drawing in which a filling process is performed from Pa11 to Pa12 is conducted. Next, drawing is conducted while the time axis is shifted to the pixel zone which is adjacent to the pixel zone of Pa11 and Pa12. After shifting, Pa22 is drawn, and drawing in which a filling process is performed from Pa22 to Pa23 is conducted. Subsequently, the drawing process is repeated in a similar manner.

Figure 7A:
FIGS. 7A and 7B are views showing examples of waveforms in the related-art example in which a weighted moving average calculating process is not performed to a waveform having a small variation, and those in the invention in which the weighted moving average calculating process is performed to a waveform having a small variation.
Figure 7B:
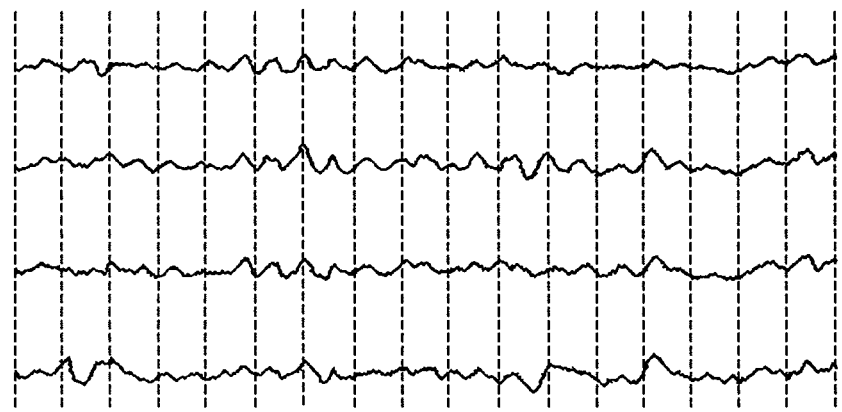

FIGS. 7A to 8B show results of the drawing processes. FIG. 7A shows waveforms in the related-art example in which the weighted moving average calculating process is not conducted, and FIG. 7B shows waveforms in the invention in which the weighted moving average calculating process is conducted. As apparent from FIGS. 7A and 7B, it can be confirmed that small noises which are not produced by an ink recorder are removed from the waveform of FIG. 7B, and the waveform is clear.

Figure 8A:
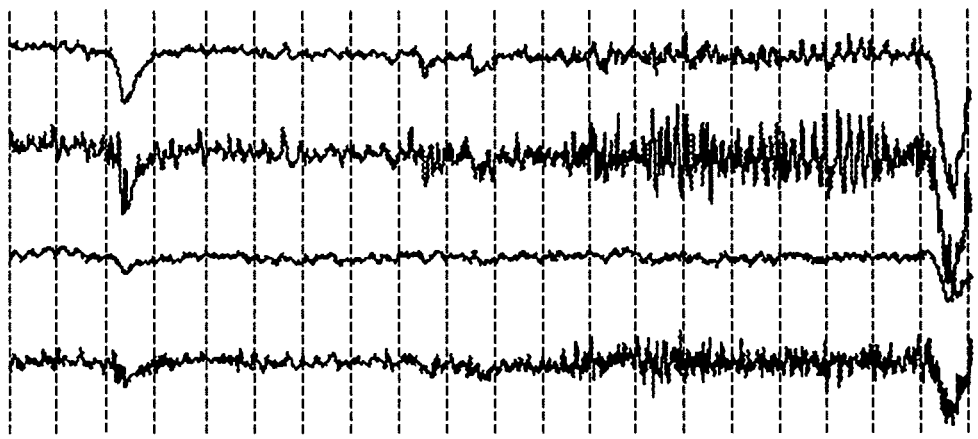
FIGS. 8A and 8B are views showing examples of waveforms in the related-art example in which the weighted moving average calculating process is not performed to a waveform having a large variation, and those in the invention in which the weighted moving average calculating process is performed to a waveform having a large variation.
Figure 8B:
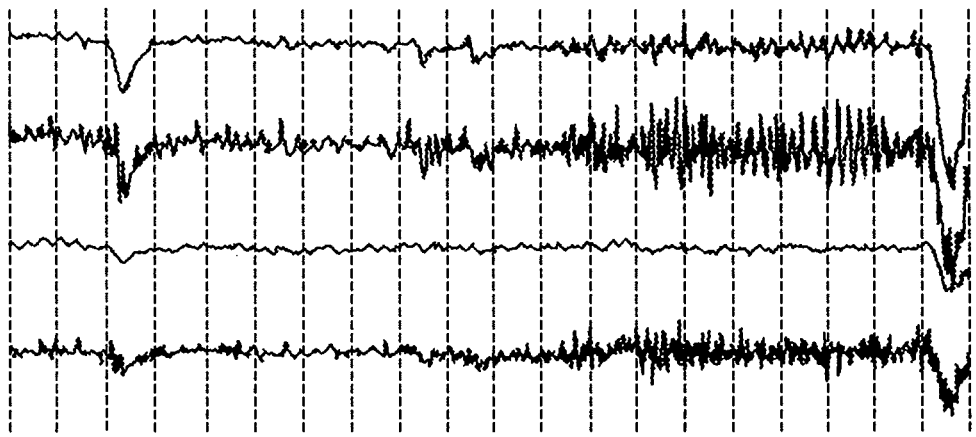

FIGS. 8A and 8B show waveforms having a large variation. FIG. 8A shows waveforms in the related-art example in which the weighted moving average calculating process is not conducted, and FIG. 8B shows waveforms in the invention in which the weighted moving average calculating process is conducted. As apparent from rear half portions of the second and fourth waveforms from the top of FIGS. 8A and 8B, it is shown that, in a portion where a waveform has a large variation, substantially no variation is produced by the weighted moving average calculating process, and necessary information related to variations is not eliminated. As apparent from a comparison of the third waveforms from the top of FIGS. 8A and 8B, it can be confirmed that minute fluctuations are removed from a waveform having a small variation.

According to the embodiment, as described above, smoothing can be strongly applied to a portion where the variation of the waveform is small, and weakly applied to a portion where the variation of the waveform is large. Therefore, minute fluctuations which are produced in a waveform characteristic of a digital image can be removed without removing a change which is characteristic of a biological signal waveform, and a waveform which is close to a waveform drawn on recording paper can be drawn.

Figure 9A:
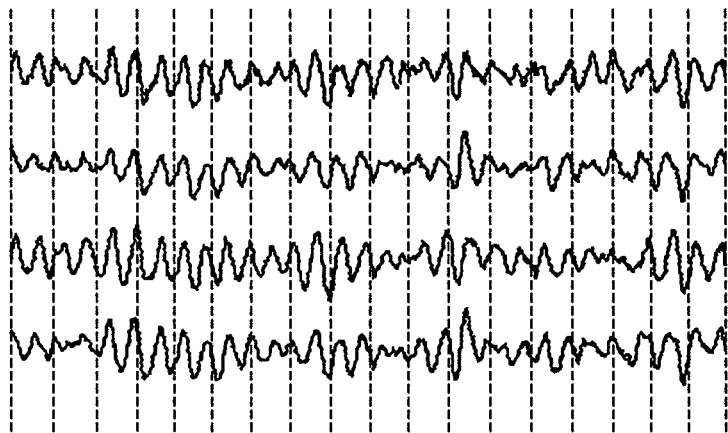
FIGS. 9A and 9B are views showing examples of waveforms which are obtained by conducting a drawing process without performing antialiasing, and those which are obtained by conducting a drawing process with performing antialiasing.
Figure 9B:
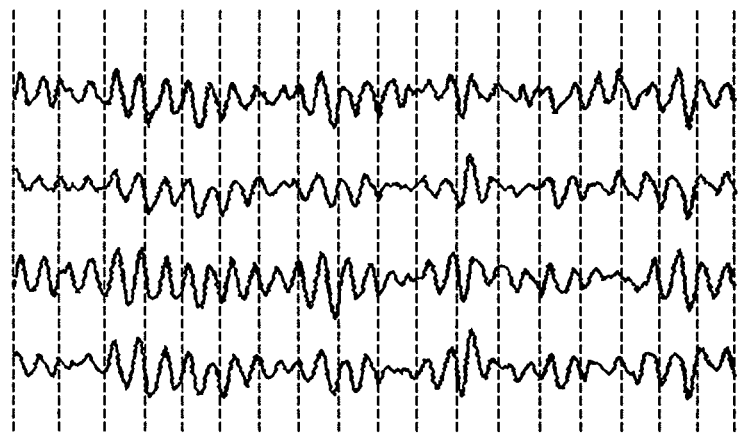

After step S15, as shown in FIG. 4, antialiasing is performed to perform an operation of controlling the display (S16: antialiasing step). FIGS. 9A and 9B show waveforms (FIG. 9A) which are obtained by conducting a drawing process without performing antialiasing, and waveforms (FIG. 9B) which are obtained by conducting a drawing process with performing antialiasing. When antialiasing is performed, jaggy of a line of a waveform can be eliminated, and it is possible to obtain a smooth and natural waveform.

Since no difference is produced between a waveform on recording paper and an electroencephalogram drawn on a displaying device or the like, there is a further effect that doctors can well interpret an electroencephalogram without feeling a sense of incongruity.

What is claimed is:

1. A biological signal drawing apparatus, drawing biological signals as drawing points in time series, the biological signal drawing apparatus comprising:
    a thinner which performs a thinning process to thin a first number of the drawing points corresponding to the biological signals sampled in each pixel zone, to obtain a second number of the drawing points for each pixel zone, the second number being smaller than the first number;
    a calculator which, after the thinning process is performed, calculates a parameter for smoothing the drawing points of the biological signal based on at least one difference of values of adjacent two of the drawing points included in a group that includes:
        a first drawing point which is a center in time series in the group and which has a first value; and
        at least one second drawing point which precedes or succeeds the first drawing point in time series and which has a second value; and
    a processor which performs a process of:
        performing a weighted moving average calculation using the first value, the second value and the calculated parameter, to obtain a third value; and
        replacing the first value of the first drawing point with the third value and displaying the third value adjacent to the second value in a smoothed biological signal waveform.

2. The biological signal drawing apparatus according to claim 1, wherein after the thinning process is performed, the drawing points in each pixel zone include drawing points having maximum and minimum values in each pixel zone.

3. The biological signal drawing apparatus according to claim 1, wherein the parameter is calculated based on an absolute value of the at least one difference of the values of adjacent two of the drawing points included in the group.

4. The biological signal drawing apparatus according to claim 1, wherein the parameter is calculated by using an exponential function.

5. The biological signal drawing apparatus according to claim 1, wherein the at least one second point includes two preceding points and two succeeding points with respect to the first point in time series, and the parameter is calculated with following calculations:

$$AbsDiff\_Sum=|Diff_{-1}|+|Diff_{-2}|+|Diff_{+2}|+|Diff_{+1}|;$$

$$AbsDiff=(AbsDiff\_Sum)^3; \text{ and}$$

$$Smooth\_Coef=0.2\ exp(-AbsDiff \times K),$$

where
the parameter is Smooth_Coef,
absolute values of differences of values of adjacent two of the preceding drawing points, the first drawing point and the succeeding drawing points are $|Diff_{-2}|$, $|Diff_{-1}|$, $|Diff_{+1}|$, and $|Diff_{+2}|$ respectively, and
a coefficient is K.

6. The biological signal drawing apparatus according to claim 5, wherein the preceding drawing points include a first preceding drawing point and a second preceding drawing point,
the succeeding drawing points include a first succeeding drawing point and a second succeeding drawing point,
the second preceding drawing point, the first preceding drawing point, the first drawing point, the first succeeding drawing point and the second succeeding drawing point are arranged in this order in time series, and
the weighted moving average calculation is performed with a following calculation:

$$V_0\_New=V_{-2} \times Smooth\_Coef + V_{-1} \times Smooth\_Coef$$

$$+V_0 \times (1-4Smooth\_Coef)$$

$$+V_{+1} \times Smooth\_Coef + V_{+2} \times Smooth\_Coef,$$

where
the first value of the first drawing point is VoNew, and
values of the second preceding drawing point, the first preceding drawing point, the first succeeding drawing point and the second succeeding drawing point are V−2, V−1, V+1, and V+2 f respectively.

7. The biological signal drawing apparatus according to claim 1, further comprising:
an antialiasing unit which performs antialiasing to the smoothed biological signal waveform drawn by the drawing points to which the process having been performed.

8. A method of drawing biological signals as drawing points in time series, the method comprising:
performing a thinning process to thin a first number of the drawing points corresponding to the biological signals sampled in each pixel zone, to obtain a second number of the drawing points for each pixel zone, the second number being smaller than the first number;
after the thinning process is performed, calculating a parameter for smoothing the drawing points of the biological signal based on at least one difference of values of adjacent two of the drawing points included in a group that includes:
a first drawing point which is a center in time series in the group and which has a first value; and
at least one second drawing point which precedes or succeeds the first drawing point in time series and which has a second value; and performing a process of:
performing a weighted moving average calculation using the first value, the second value and the calculated parameter, to obtain a third value; and
replacing the first value of the first drawing point with the third value and displaying the third value adjacent to the second value in a smoothed biological signal waveform.

9. The method according to claim 8, wherein after the thinning process is performed, the drawing points in each pixel zone include drawing points having maximum and minimum values in each pixel zone.

10. The method according to claim 8, wherein the parameter is calculated based on an absolute value of the at least one difference of the values of adjacent two of the drawing points included in the group.

11. The method according to claim 8, wherein the parameter is calculated by using an exponential function.

12. The method according to claim 8, wherein the at least one second point includes two preceding points and two succeeding points with respect to the first point in time series, and
the parameter is calculated with following calculations:

$$AbsDiff\_Sum=|Diff_{-1}|+|Diff_{-2}|+|Diff_{+2}|+|Diff_{+1}|;$$

$$AbsDiff=(AbsDiff\_Sum)^3; \text{ and}$$

$$Smooth\_Coef=0.2\ exp(-AbsDiff \times K),$$

where
the parameter is Smooth_Coef,
absolute values of differences of values of adjacent two of the preceding drawing points, the first drawing point and the succeeding drawing points are $|Diff_{-2}|$, $|Diff_{-1}|$, $|Diff_{+1}|$, and $|Diff_{+2}|$, respectively, and
a coefficient is K.

13. The method according to claim 12, wherein the preceding drawing points include a first drawing preceding point and a second drawing preceding point,
the succeeding drawing points include a first succeeding drawing point and a second succeeding drawing point,
the second preceding drawing point, the first preceding drawing point, the first drawing point, the first succeeding drawing point and the second succeeding drawing point are arranged in this order in time series, and
the weighted moving average calculation is performed with
a following calculation:

$$V_0\_New=V_{-2} \times Smooth\_Coef + V_{-1} \times Smooth\_Coef$$

$$+V_0 \times (1-4Smooth\_Coef)$$

$$+V_{+1} \times Smooth\_Coef + V_{+2} \times Smooth\_Coef,$$

where
the first value of the first drawing point is VoNew, and
values of the second preceding drawing point, the first preceding drawing point, the first succeeding drawing point and the second succeeding drawing point are $V_{-2}$, $V_{-1}$, $V_{+1}$, and $V_{+2}$, respectively.

14. The method according to claim 8, further comprising:
performing antialiasing to the smoothed biological signal waveform drawn by the drawing points to which the process having been performed.

* * * * *